(12) United States Patent
Iwatschenko et al.

(10) Patent No.: US 8,910,627 B2
(45) Date of Patent: Dec. 16, 2014

(54) APPARATUS FOR THE AEROSOLIZATION OF LARGE VOLUMES OF DRY POWDER

(75) Inventors: Peter Iwatschenko, Neunkirchen am Brand (DE); Gerhard Pohlmann, Meerbeck (DE); Horst Windt, Burgwedel (DE); Wolfgang Koch, Steimbke (DE); Michel Kist, Hausen (AT)

(73) Assignee: Takeda GmbH, Constance (DE)

( * ) Notice: Subject to any disclaimer, the term of this patent is extended or adjusted under 35 U.S.C. 154(b) by 244 days.

(21) Appl. No.: 13/264,422

(22) PCT Filed: Apr. 22, 2010

(86) PCT No.: PCT/EP2010/055345
§ 371 (c)(1),
(2), (4) Date: Nov. 30, 2011

(87) PCT Pub. No.: WO2010/122103
PCT Pub. Date: Oct. 28, 2010

(65) Prior Publication Data
US 2012/0090606 A1    Apr. 19, 2012

(30) Foreign Application Priority Data
Apr. 23, 2009    (EP) .................................... 09158625

(51) Int. Cl.
*A61M 16/10*    (2006.01)
*A61M 11/02*    (2006.01)
(Continued)

(52) U.S. Cl.
CPC ........... *A61M 15/0065* (2013.01); *A61M 11/02* (2013.01); *A61M 15/0005* (2014.01); *A61M 11/001* (2014.01); *A61M 11/06* (2013.01); *B05B 7/1413* (2013.01); *A61M 2205/07* (2013.01); *A61M 16/0808* (2013.01); *A61M 2202/064* (2013.01); *A61M 16/202* (2014.01); *B05B 7/1422* (2013.01); *A61M 15/0086* (2013.01)
USPC ............ 128/203.12; 128/200.14; 128/203.15; 128/204.18

(58) Field of Classification Search
USPC .......................... 128/203.12, 204.18, 204.21, 128/200.14–200.23, 203.19; 222/198, 222/200–203, 207, 209
See application file for complete search history.

(56) References Cited

U.S. PATENT DOCUMENTS 2,792,262 A * 5/1957 Hathorn ......................... 406/146
5,160,072 A * 11/1992 Nye .............................. 222/463
(Continued)

FOREIGN PATENT DOCUMENTS

FR    2 598 918 A1    11/1987
GB    24 848    3/1914
(Continued)

*Primary Examiner* — Valerie L Skorupa
(74) *Attorney, Agent, or Firm* — Nath, Goldberg & Meyer; Jerald L. Meyer; Sheldon M. McGee

(57) ABSTRACT

The claimed subject matter relates to a device for dosing and aerosolization of aerosolizable material. The device comprises: a body with an aerosolization channel with a distal attachment portion connectable to a source of carrier gas which provides pressure pulses to the aerosolization channel; a proximal attachment portion for outputting aerosolized material and a reservoir for receiving aerosolizable material. The reservoir comprises walls and is connected in a gas-tight manner to the body and in fluid connection with the aerosolization channel. At least part of the walls of the device are self-exciting membranes that can be put into oscillation by the pressure pulses.

15 Claims, 4 Drawing Sheets

(51) Int. Cl.
*A61M 11/06* (2006.01)
*A61M 15/00* (2006.01)
*A61M 11/00* (2006.01)
*A61M 16/20* (2006.01)
*B05B 7/14* (2006.01)
*A61M 16/08* (2006.01)

(56) References Cited

U.S. PATENT DOCUMENTS

| | | | | |
|---|---|---|---|---|
| 5,178,138 | A | * | 1/1993 | Walstrom et al. ........ 128/200.23 |
| 5,673,686 | A | | 10/1997 | Villax et al. |
| 5,921,369 | A | * | 7/1999 | Steele .......................... 193/25 R |
| 7,530,353 | B2 | * | 5/2009 | Choncholas et al. .... 128/204.18 |
| 2003/0164169 | A1 | * | 9/2003 | Stangl et al. ............. 128/203.12 |
| 2005/0224076 | A1 | * | 10/2005 | Pfichner et al. .......... 128/200.14 |
| 2006/0162723 | A1 | * | 7/2006 | Selzer et al. ............. 128/200.14 |
| 2007/0283954 | A1 | * | 12/2007 | Dhuper et al. ........... 128/203.12 |
| 2008/0264420 | A1 | * | 10/2008 | Brown ...................... 128/205.24 |
| 2008/0308096 | A1 | * | 12/2008 | Borgschulte et al. .... 128/200.14 |
| 2009/0235925 | A1 | * | 9/2009 | Power et al. ............. 128/200.14 |
| 2011/0139150 | A1 | * | 6/2011 | Gallem et al. ........... 128/200.14 |
| 2011/0146670 | A1 | * | 6/2011 | Gallem et al. ........... 128/200.14 |

FOREIGN PATENT DOCUMENTS

| | | |
|---|---|---|
| WO | 02/13896 A1 | 2/2002 |
| WO | 2006/108558 A1 | 10/2006 |
| WO | 2008/034504 A2 | 3/2008 |

* cited by examiner

APPARATUS FOR THE AEROSOLIZATION OF LARGE VOLUMES OF DRY POWDER

This is a National Phase Application filed under 35 U.S.C. §371 as a national stage of PCT/EP2010/055345, filed on Apr. 22, 2010, an application claiming the benefit under 35 U.S.C. §119 of European Patent Application No. 09158625.5, filed on Apr. 23, 2009, the content of each of which is hereby incorporated by reference in their entirety.

The invention relates to a device for dosing and aerosolization of aerosolizable material, in particular powdery medical substances such as, e.g., pharmaceutical preparations for inhalation. The device is particularly suited for the aerosolization of powdery lung surfactant preparations.

BACKGROUND OF THE INVENTION

Devices for aerosolization ("dry nebulization") of aerosolizable ("nebulizable") dry material are known to the skilled person. For example, for the aerosolization of powdery pharmaceutical preparations, so-called dry powder inhalers (DPIs) have been described. In these devices, an aerosolizable material, for example a powdery medical substance, is acted upon by a compressed gas or carrier gas in a specially provided chamber and, within this chamber, is converted to a state which is referred to as aerosol or dry mist. The particles of the material are in this case present in a preferably uniform and finely dispersed form across the entire volume of compressed gas or carrier gas and are then discharged from the chamber in this state via suitable devices.

Such devices can be used for administration of medical substances to spontaneously breathing or ventilated patients. For use in spontaneously breathing patients, the devices are generally connected to a suitable mouthpiece or a breathing mask. In invasive use, i.e. on ventilated patients, these devices feed the aerosolized medical substance into a ventilator system which then delivers the aerosolized material to the patient's lung.

In the devices known hitherto for aerosolization of powdery material, however, the problem generally found was that large amounts of medical substances could be delivered to the patient only, if at all, with considerable outlay in terms of equipment, for example using extensive mechanical dosing devices. Generally, the known devices were suitable for the aerosolization of pharmaceutical quantities in the range from approximately 1 µg up to approximately 20 mg. However, certain medical substances such as, e.g., lung surfactant preparations, require administration of large amounts, for example more than 100 mg or even in the gram range which, when using conventional DPIs, requires very long inhalation times. A second problem of devices known from the art can be the reproducibility of the amount of aerosolized material delivered to the patient. This is particularly the case when during storage or even during action of the inhaler the particles of the aerosolizable material agglomerate to larger particles with a different aerodynamic behaviour. Large particles will have a much smaller chance to reach their target, the deeper lung, since they tend to be deposited in the upper airways or throat or even somewhere in the inhaling apparatus.

The problem of administering large amounts of aerosolizable material such as lung surfactant preparations in precise doses concerns all sections of the apparatus used for inhalation: the air supply and its controller, the aerosolizing unit itself, the piping and valve system (including, where appropriate, the inner surfaces of a ventilator system), and the respiratory endpieces (mask, tube), in other words all sections in which an uncontrolled loss by unwanted deposition of aerosolized particles and thus reduction of the dose delivered to the patient and obstruction may occur.

In conventional aerosolizing units, one problem generally found was that the aerosolizable material, which is present as a loose charge in a storage container, for example a commercially available pharmaceutical vial, tends to agglomerate, by reason of its surface quality and/or its moisture content, which can result in blockage of a comparatively narrow aperture cross section of the vial. Such agglomeration may also occur in lung surfactant preparations. Such blockages can normally be obviated only by suitable mechanical means, in order to ensure a continuous dosing of the aerosolizable material over quite a long period of time. In addition, as already pointed out above, agglomerated particles of aerosolizable material, for example lung surfactant preparations, are not generally able to access the lungs with the same efficiency and following the same local distribution/deposition pattern as smaller, non-agglomerated particles.

In the prior art aerosolizing unit of GB 24 848 A, a reservoir of aerosolizable material is connected via a narrow passage to a chamber into which supply air is pressed by means of a syringe. Deagglomeration of the aerosolized particles takes place as the supplied air is further forced into the reservoir and performs a whirling action therein; where after the dispersed aerosolizable material is expelled through the chamber and out of a nozzle towards the patient. In FR 2 598 918 A the aerosolizable material is, in contrast, conveyed by an Archimedean screw into a jet of compressed air where dispersion takes place.

In many instances it is necessary to ensure rapid and high-dose administration of aerosolizable material, in a form accessible to the alveoli, into the lungs with a constant dosage, in rapid sequence and over a period of several minutes. Both above-mentioned systems cannot, however, provide administration of high doses of aerosolizable material and are, due to their geometry and dispersion mechanism, still prone to agglomeration, e.g. in the chamber or in the hopper provided with the screw, so that accurate dosing remains an issue. In fact, such administration was possible, if at all, only with considerable outlay in terms of equipment.

WO 2006/108558 A1 discloses a device for dosing and powder aerosolization in which deagglomeration of the aerosolizable material, such as a powdery lung surfactant preparation, is achieved by means of pressure compensation between the pressure pulses sent into the aerosolization channel of the device. The shear force necessary for deagglomeration is created by taking advantage of the high pressure during the pulses. While this system delivers superior results over the known prior art systems in terms of concentration of aerosolized material delivered, issues of concern remain regarding residues of aerosolizable material adhering to the inner surfaces of the system such as the reservoir walls or the bottom of the aerosolization channel.

A further issue concerns the output characteristics of a dosing device such as the one disclosed in WO 2006/108558 A1. As the dosing device uses pressure pulses to deagglomerate, the question arises about the effect these may have on the patient. The pressure pulses are of substantial magnitude and, thus, the dosing device cannot be connected directly to the patient's breathing front ends such as masks in the case of spontaneously breathing patients. For ventilated patients, the output of the dosing device must be connected to the ventilator in order to allow for both adequate and precise dosage, and for the necessary oxygen supply. In the case of infants, moreover, the volume and dosage of the supplied aerosol as well as the partial pressure of oxygen as well as the airway pressure are even more critical than in adults and need special consideration. Since for infants the conventional approach of supplying airborne drugs via pressure respirators and tubes is extremely stressful, specialized equipment and rooms are required.

SUMMARY OF THE INVENTION

It is therefore an object of the present invention to provide a device for dosing and aerosolization of aerosolizable dry material which overcomes the above problems of residues of aerosolizable material and allows essentially all the aerosolizable material present in the device to be aerosolized and delivered to the patient, thereby allowing for a yet unachieved dosing accuracy also in the case in which large volumes of dry powder need to be administered.

Since the utility of the device according to the invention is not limited to the dosing and aerosolization of substances used in a medical context, such as substances used for diagnostics and/or for treatment, it is a further object of the invention to provide a device for dosing and aerosolization of aerosolizable dry material which overcomes the above problems of residues of aerosolizable material and allows essentially all the aerosolizable material present in the device to be aerosolized.

It is also an object of the invention to provide a system for dosing and aerosolization of aerosolizable dry material which allows treatment of spontaneously breathing as well as ventilated patients and can be used both with adults and infants.

These objects are achieved by means of a device for dosing and aerosolization of aerosolizable dry material according to claim 1. Further optional and preferred embodiments are defined in the respective dependent claims.

In a first aspect of the invention, the novel device for dosing and aerosolization of aerosolizable dry material comprises a body with an aerosolization channel having a distal attachment portion connectable to a source of pulsed carrier gas which provides pressure pulses of the gas to the aerosolization channel and a proximal attachment portion for outputting aerosolized material (the "aerosol") towards a patient, and a reservoir for receiving aerosolized material ("proximal" and "distal" as seen from the patient). It is further preferred that the device has an attachment portion connectable to a source of non-pulsed carrier gas serving to transport the generated aerosol from the aerosolization channel or from the reservoir towards the patient. The reservoir comprises walls and is connected in a gas-tight manner to the body and is in flow connection with the aerosolization channel. At least parts of the walls are membranes that can be put into oscillation. While the latter could be realized by any sort of actuator, it is preferred that the membranes are self-exciting membranes that can be put into oscillation by the pressure pulses.

Preferably, the novel device comprises means for transferring oscillation energy between different areas of the membranes. Advantageously said means can recircle oscillation energy induced by the pressure pulses. It is preferred to transfer the oscillation energy from stronger oscillating areas of the membranes to weaker oscillating areas. This serves to compensate for pressure differences between the membranes. Thus activating weaker oscillating areas. Such a transfer can be assured for example by a tubing connecting the proximal attachment portion and/or the aerosolization channel and the distal reservoir of the device.

The term "membrane" as used herein refers to any sheet-like structure that is impermeable to gas, liquid and the aerosolizable material, and that forms at least part of the containment for the aerosolizable material in the reservoir. "Self-exciting" as used herein refers to the property of the membrane to elastically deform and oscillate in response to pressure pulses of the carrier gas supplied to the device. As such it is to be understood that, as a function of the membrane's material, the membrane needs to be thin and flexible enough in order to be deformed by the pressure pulses. Examples of membrane materials are elastic polymers such as silicone, but other materials will be apparent to the skilled person.

By being provided with membrane walls, the inventive device is capable of utilising essentially the complete amount of aerosolizable dry material stored in the reservoir and transform it into an aerosol because the oscillation of the membrane walls of the reservoir loosens up aerosolizable material, so it can fall into the dosing chamber beneath the reservoir. The process of aerosolization is, for example, described in WO 2006/108558.

According to the invention it is thus possible to have a uniformly loose charge of aerosolizable dry material available in the device for dosing and aerosolization after each pressure pulse, as a result of which a gradually increasing compaction of the material is avoided and a uniform dosing is guaranteed over a considerable time period. The device according to the invention thus easily allows aerosolizable material to be dosed in large amounts in a highly reproducible manner and preferably without moving parts. In addition, during the pressure compensation between aerosolization channel and reservoir, a loosening of the charge of the aerosolizable material is achieved. It is thus possiblethat the mixture of compressed carrier gas and material predominantly contains deagglomerated particles, preferably exclusively or almost exclusively particles having the size of the primary, non-agglomerated particles of the aerosolizable material. If the aerosolizable material is in the form of a powdery medical substance such as, e.g., powdery lung surfactant, it is possible that the primary particles of the medical substance located in the reservoir are present in the mixture of compressed gas and material. To this extent, the device according to the invention permits, preferably completely free of mechanical moving parts, optimal aerosolization of the aerosolizable dry material even down to the size of the primary particles.

In the preferred case that the device is used for dosing and aerosolization of substances for therapeutic and/or diagnostic purposes, the size of the primary particles of the aerosolizable material preferably corresponds to a mass median aerodynamic diameter (MMAD) which is such that the particles are able to access the lungs, i.e. the site of action in the airways or the alveoli of the lungs. The MMAD of particles that can access the lungs is in the range of 1 to 5 µm. The desired MMAD range, according to the invention, of the particles in the mixture of compressed gas and material is consequently 1 to 5 µm.

Preferably, a funnel portion tapered towards the aerosolization channel is provided in the body between the reservoir and the channel, and the walls of the funnel portion are self-exciting membranes. The funnel portion is where the aerosolizable material falls to and accumulates from the reservoir before entering the aerosolization channel. The differential pressure pulses generated as a result of the pressure pulses utilizing the Venturi principle create a pressure gradient which serves to suck the aerosolizable material into the aerosolization channel and entrains it into the carrier gas stream, by this generating a highly concentrated aerosol. As the walls of the funnel portion are self-exciting membranes, no material accumulated in the funnel portion will be left adhering to its walls and substantially all of it can be entrained in the carrier gas.

The reservoir may preferably be provided with a lid that comprises a membrane towards the reservoir. While the cover as such allows the reservoir to be (re)filled, the membrane on the cover will also oscillate and support a complete deagglomeration and detachment of aerosolizable material from the inner surfaces of the reservoir. If desired, between membrane and lid a gas- and/or humidity absorber can be inserted.

Additionally, a self-exciting membrane may be provided as part of the bottom of the aerosolization channel beneath the connection thereof with the reservoir. When aerosolizable material falls into the aerosolization channel, not all of it is always immediately entrained in the carrier gas stream, and some material may deposit and accumulate beneath the mentioned connection. By providing this area with a self-exciting membrane, the pressure pulses sent through the aerosolization channel excite this membrane to oscillate so that the material is reentrained in the carrier gas. This configuration can be termed a "passively controlled" membrane. It is also conceivable to dispose an actuator connected to the membrane so as to drive the membrane to oscillate. This is called "actively controlled".

Finally, it is preferred that the reservoir and the body are integrally formed. This has the advantage that a disposable device can be provided in which the total dose of aerosolizable material is carefully controlled by the manufacturer and contamination and wrong dosage due to filling inaccuracies can be prevented.

In a second aspect of the invention, a system for dosing and aerosolization of aerosolizable dry material comprises the above-described device for dosing and aerosolization of aerosolizable dry material. In addition, a first hollow spacer is connected to the proximal attachment portion of the device and comprises a distal portion having inner walls tapered towards the proximal attachment portion, and a proximal portion having inner walls tapered towards the patient, with preferably a central cylindrical portion there between.

The term "spacer" as used herein refers to an additional piece of pathway for respiratory or carrier gas/aerosol to traverse, which introduces expansion space for the pulsed gas stream. The geometry of the first hollow spacer allows to dampen the pressure pulse of the gas carrying the aerosol to the patient and to reduce at the same time the associated noise, much in the same way as a silencer. Thus, both for spontaneously breathing and for ventilated patients, the aerosol arrives more uniformly and without unacceptable pressure spikes.

According to a preferred embodiment, the inner walls of the distal portion, the central portion and/or the proximal portion of the first hollow spacer comprise self-exciting membranes. When a differential pressure pulse arrives in the system, the membranes oscillate due to their elasticity so that this construction avoids that particles from the aerosol adhere to and stay on the walls of the spacer.

It is also preferred that an annular gap is provided between the distal and the central portions of the first hollow spacer, which is connectable to an auxiliary air supply. This annular gap can be supplied with auxiliary air that rinses the inside of the spacer and makes sure no residue of aerosolizable material stays adhered to the wall. It is most preferred that the geometry of the annular gap allows formation of a sheath flow of auxiliary air along the walls of the cylindrical part of the spacer, thus ensheathing the aerosol stream entering the spacer and efficiently helping to avoid the aerosolized particles to deposit on the spacer's walls.

In a preferred embodiment, the system according to the second aspect of the invention further comprises a second hollow spacer connected to the proximal portion of the first hollow spacer and distally to a patient connector, the second hollow spacer having an ambient air inlet with a non-return valve provided at the distal end and an exhaled gas outlet provided at the proximal end of the second hollow spacer. The second hollow spacer preferably has a larger cross-section and volume than the preceding first hollow spacer, and may preferably be cylindrical, although the invention does not provide any limitation on shape.

This arrangement is particularly advantageous for administration of aerosolized material to spontaneously breathing patients. Like the first hollow spacer, the second hollow spacer serves to attenuate the differential pressure pulses coming from the supply of compressed air through the dosage and aerosolization device and to reduce the associated noise. But it also has the function of providing an intermediate storage for the aerosol, that is the aerosolized material entrained in the carrier gas. From this intermediate storage, which is connected to the patient's mouth piece, a spontaneously breathing patient can inhale the predetermined dose of aerosolized material. Due to the expanded cross-section and larger volume of the second hollow spacer with respect to the first hollow spacer, the negative respiratory pressure necessary to draw and inhale the aerosolized material from the second hollow spacer does not become excessive as would be the case if the dosage and aerosolization device and first hollow spacer were directly connected to the patient. Moreover, inhalation of aerosolized material from the first or second spacer is further facilitated by the provision of auxiliary air as described above.

In an alternative preferred embodiment, the aerosolization device is connected to a ventilator system operated as CPAP System (continuous positive airway pressure) delivering ventilatory support to a patient. In such a setup, the aerosol is introduced into a ventilator or CPAP system via a T-connector to a patient side respiratory front end. This system provides numerous advantages to patients on mechanical ventilation or on ventilatory support, in particular in case of infants and neonates. In acute situations, these little patients may need carefully controlled administration of aerosolized medical substances. By connecting the ventilator or CPAP system and the dosing and aerosolization device via a T-connector that is connecting the device in parallel to the respirator, it is possible to control both how much air or oxygen is provided from the ventilator (by controlling the air and/or oxygen pressure) and, separately, how much aerosolized material is provided to the patient. Furthermore, in contrast to delivery of the aerosol into the inspiration branch of the respirator, this configuration allows for higher aerosol concentrations in the gas delivered to the patient since dilution is minimized.

As mentioned above means can be provided to transfer oscillation energy from one area of the membranes to another.

Preferably, a compensation tubing is provided between the interior of the first hollow spacer and the interior of the funnel portion. This tubing serves to compensate for pressure differences between spacer and reservoir and at the same time to activate the funnel membrane.

The above-described systems may be integrated in standard ventilator systems for routine administration/addition of aerosolizable material, such as lung surfactant, to the respiratory gas.

It is obvious to the person skilled in the art that the aerosolization device as described hereinabove can be used in a variety of technical fields. Actually the device according to the invention will be applicable whenever efficient and uniform aerosolization of powders is desired. While preferred uses of the device according to the invention are in the field of therapy and administration of inhalable drugs, pharmaceutical preparations and other medical substances, in particular lung surfactant, the device will be useful for the aerosolization of any sort of aerosolizable substances in the range of less than 100 mg up to several grams of substance. It is even conceivable that an adequately sized version of the device allows aerosolization of even higher amounts of substances up to technical scales. The particle size or particle size distribution of the material to be aerosolized will depend on the particular application. For example, as is known from the art, particles to be administered to the lung by inhalation ideally will have a size in the range of 1-5 µm MMAD. Of course, the device according to the invention is not limited to aerosolization of particles in this size range. Rather, smaller as well as larger particles would lend themselves for aerosolization by use of this device. To give an example, powder coating of workpieces which has gained considerable importance in recent years would be a possible application where relatively large quantities of particles having a very small size (e.g., <1 µm) have to be aerosolized.

Accordingly, the present invention relates to a device for dosing and aerosolization of aerosolizable material comprising a body with an aerosolization channel having a distal attachment portion connectable to a source of carrier gas which provides pressure pulses of the gas to the aerosolization channel and a proximal attachment portion for outputting aerosolized material towards a patient, a reservoir for receiving aerosolizable material, the reservoir comprising walls and being connected in a gas-tight manner to the body and in fluid connection with the aerosolization channel, characterized in that at least part of the walls are self-exciting membranes that can be put into oscillation by the pressure pulses.

The present invention also relates to the above device, wherein a funnel portion tapered towards the aerosolization channel is provided in the body between the reservoir and the channel, and wherein walls of the funnel portion are self-exciting membranes.

The present invention also relates to any of the above devices, wherein the reservoir is provided with a top cover and the top cover comprises a self-exciting membrane towards the reservoir.

The present invention also relates to any of the above devices, wherein a self-exciting membrane is provided in a wall of the aerosolization channel beneath the connection thereof with the reservoir.

The present invention also relates to any of the above devices, wherein the reservoir and the body are integrally formed.

The present invention also relates to any of the above devices, wherein the reservoir is connected with the aerosolization channel via a valve. In one embodiment, the valve is a rotary valve.

In summary the present invention uses the energy of a pressure pulse generated for example by expansion of compressed gas to excite elastic elements. As mentioned before, these elements can be membranes, especially self-exciting membranes. By exciting the membranes energy is taken up from the original pressure pulse, thus weakening this pressure pulse. As a result the aerosolizable material is aerosolized in a more continous, constant and homogeneous form compared to a rapid output initiated by an unweakened pressure pulse. By such an attenuation of the pressure pulse the aerosole produced is comfortable breathable by a patient.

Additionally an agglomeration of the aerosolizable material, especially in the reservoir, is prevented.

DETAILED DESCRIPTION OF PREFERRED EMBODIMENTS

Figure 1:
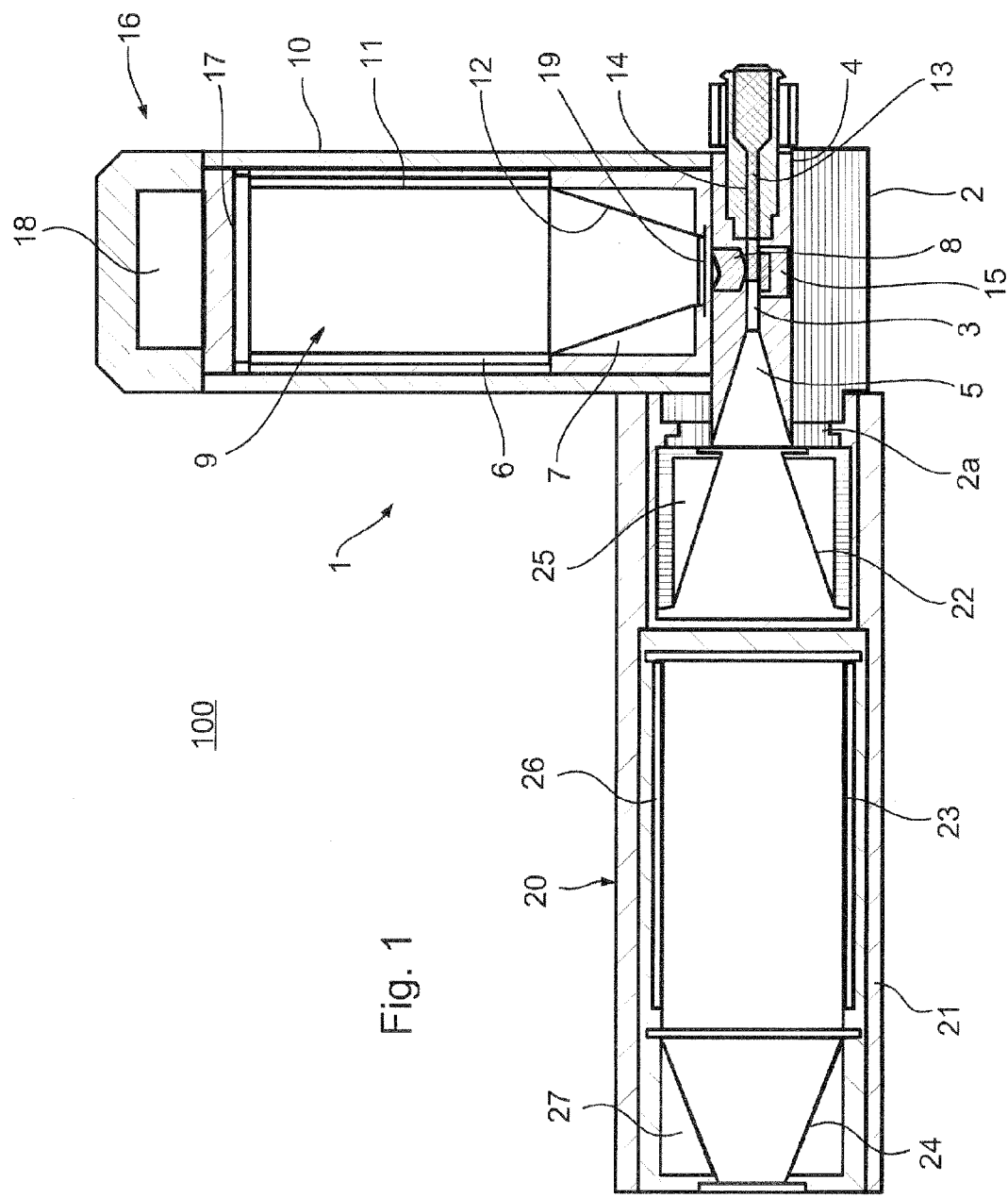
FIG. 1 is a longitudinal sectional view of an embodiment of a system for dosing and aerosolization according to the invention.

In FIG. 1, a longitudinal sectional view of a first embodiment of the system for dosing and aerosolization is shown. The system 100 comprises a device 1 for dosing and aerosolization, in which an aerosolization channel 3 is arranged inside a body 2. At its distal end (on the right in FIG. 1), the body 2 comprises a capillary seat 4 into which a capillary tube holder 14 supporting a capillary tube 13 is fitted. This capillary tube holder 14 can in turn be connected via connecting lines and a valve (both not shown) to a supply of pulsed compressed carrier gas. At its proximal end (on the left in FIG. 1), the aerosolization channel 3 opens into a dispersing nozzle 5 whose cross section increases continuously in a direction extending away from the capillary tube 13.

Above the aerosolization channel 3, the device 1 comprises a reservoir 9 for the powdery material to be aerosolized. The reservoir 9 comprises an outer wall 10 and an inner portion having a cylindrical wall 11 and conically tapering wall 12. The walls 11 and 12 are self-exciting membranes made of, e.g., medical grade silicone having a wall thickness of about 0.5 mm. Between the outer wall 10 and the cylindrical and conical walls 11 and 12, spaces 6 and 7 are respectively formed. At the bottom, the reservoir 9 forms an aperture 19 located above the aerosolization channel 3 that is partially integral part of the dosing chamber 8. Located above this aperture 19 will be a charge of the powder to be aerosolized (not shown) which may be clumped together to such an extent that almost no grain of aerosolizable material enters the aerosolization channel 3. The whole assembly consisting of parts 5, 3, 15, 8, 13, and 4 may be turned by 90 degrees around the apparatus' longitudinal axis to prevent powder from falling into the chamber 8, thus closing the reservoir. Accordingly, said assembly together with the body 2 forms a rotary valve which allows to interrupt supply of the powder stored in the reservoir 9 to the dosing chamber 8 and aerosolization channel 3.

On top of the reservoir 9, a lid 16 is provided that tightly closes the reservoir. At the bottom side of the lid, towards the interior of the reservoir, a self-exciting membrane 17 is provided that seals the top opening of the reservoir 9. Above the membrane, a humidity (or generally gas) absorber 18 is included in the cover that eliminates residual humidity or other trace gases in the reservoir which otherwise could have adverse effects. Furtheron, a space is formed between the membrane 17 and the humidity absorber 18 (not shown).

In the present embodiment, the reservoir 9 and the body 2 with the aerosolization channel 3 are integrally formed, whereby complete gas-tightness and sterility is guaranteed. However, it is to be understood that they may also be separate elements that are fitted together in an gas-tight manner.

The dispersing nozzle 5 opens into a proximal attachment piece 2a which is an integral component part of the body 2. Onto the attachment piece 2a, a hollow spacer 20 is fitted in a gas-tight manner. The spacer 20 comprises a cylindrical outer wall 21, a distal portion with conical inner walls 22 tapered distally, a proximal portion with conical inner walls 24 tapered proximally, and a central portion having cylindrical walls 23 arranged there between. As with the reservoir, also the walls 22, 23, 24 of the spacer 20 are self-exciting membranes made of, e.g., silicone. Between the outer wall 21 and walls 22, 23, 24 corresponding spaces 25, 26, 27 are provided. An annular gap is formed between the distal and central portions of the spacer 20 and is connected to an auxiliary gas supply (not shown).

In operation, pressure pulses of carrier gas enter the aerosolization channel 3 of device 1 through the capillary 13 and, due to the pressure difference created between the gas exiting from capillary 13 and the reservoir 9 by Venturi's principle, aerosolizable material is sucked from the reservoir 9 into the aerosolization channel 3, dispersed and entrained in the carrier gas. At the same time, this differential pressure pulse also acts on the membrane walls 11, 12 of the reservoir 9 and the membrane walls 22, 23, 24 of the spacer 20, causing them to bulge and oscillate according to the frequency of the pressure pulses. Thus, aerosolizable material adhering to the walls is reentrained into the bulk material and free to enter the carrier gas stream.

It is to be understood that in alternative embodiments only some of the inner walls of the device are carried out as self-exciting membranes. For example, in an alternative embodiment only the tapered wall 12 is a self-exciting membrane. Obviously, each inner wall of the device which is not carried out as self-exciting membrane does not require a hollow space between this inner and the corresponding outer wall. For example, when only the tapered wall 12 is carried out as self-exciting membrane, spaces 6 and 25-27 are dispensable.

The amount of aerosolizable material that can be administered with the devices and systems of the present invention exceeds 50 mg and is coupled with a high precision of dosage. On one hand, the precision allows the use of drugs having a very narrow "therapeutic window" and on the other hand the large volumes make the system suitable for use with substances that need to be administered in large quantities. For example, aerosolizable medical substances other than lung surfactant which can be administered by use of the device according to the invention include antibiotics, nucleic acids, retard formulas, peptides/proteins, vaccines, antibodies, insulin, osmotically active substances like mannitol, hydroxyethyl starch, sodium chloride, sodium bicarbonate and other salts, enzymes (e.g., DNAse), N-acetyl cystein, etc.

Figure 2:
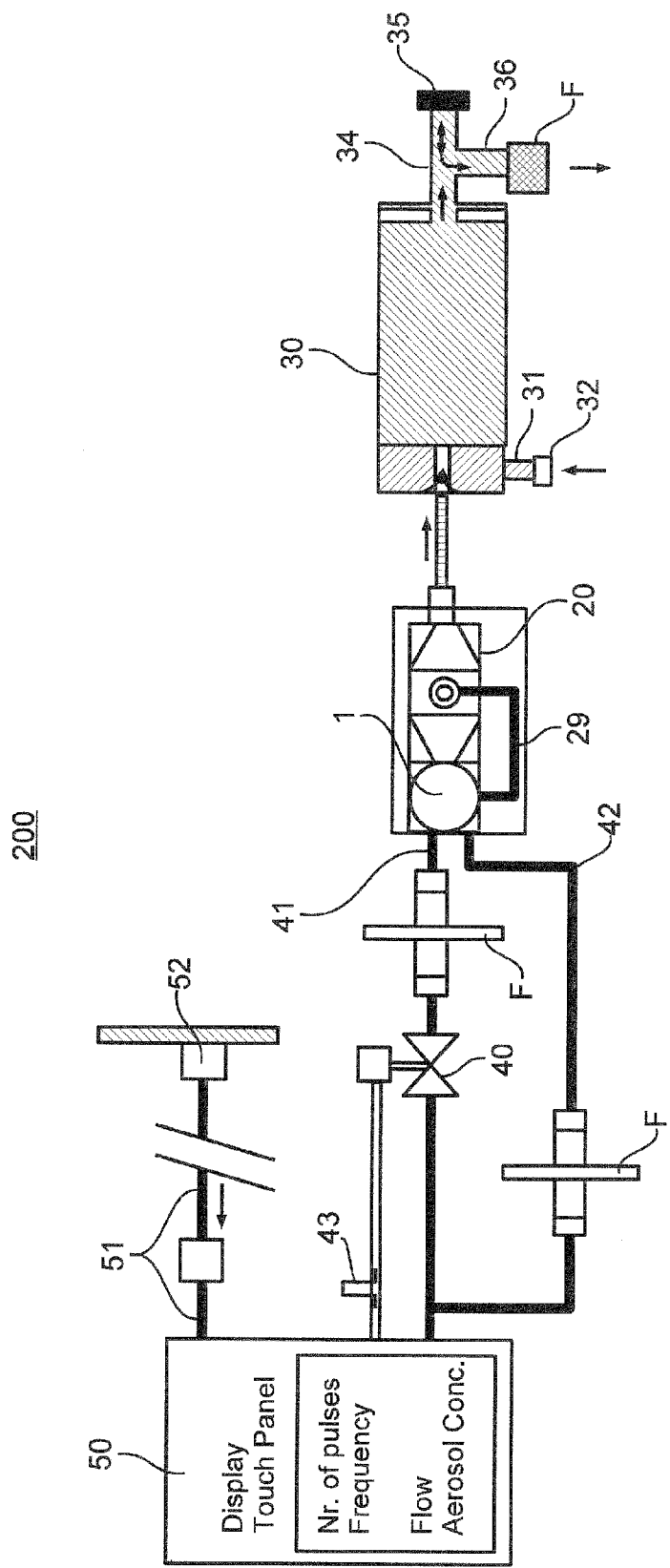
FIG. 2 is schematic view of an embodiment of a system for dosing and aerosolization for use with spontaneously breathing adult patients.

Turning now to FIG. 2, an embodiment of a system for dosing and aerosolization 200 is shown, which is employed for large volume dry powder inhalation of spontaneously breathing patients. The system 200 comprises the device 1 for dosing and aerosolization and the first spacer 20 of the first embodiment, wherein additionally a compensation tubing 29 connects the spaces 6, 7 of the reservoir with spaces 25, 26, 27 of the spacer 20. On the upstream side, the system 200 comprises a controller 50 that is connected via a compressed air line 51 to a compressed air supply 52 (e.g., the compressed air supply of a hospital) providing the compressed air through a main connecting line 41 to the dosing and aerosolization device 1. The main connecting line 41 is connected to the capillary holder 14 (distal attachment portion) of the device 1. The flow of the compressed air to the device is regulated by a fast-switching solenoid valve 40 which is caused to open and close by a current pulse 43 sent from the controller so as to achieve a determined number, duration and frequency of air pressure pulses. In use, the flow of compressed air may be triggered automatically by the controller, but may also be triggered by the breathing of the patient so as to adapt the timing of aerosolization and the volume of aerosolized material provided in the second spacer to the patient's breathing characteristics.

An auxiliary connecting line 42 supplies un-pulsed air to the annular gap 28 of the spacer 20 (the connection is not shown) to thereby flush the spacer of residues of aerosolizable material. Both connecting lines 41 and 42 comprise filters F to block contamination by undesired particles.

On the downstream side, a second spacer 30 is connected to the first spacer 20. At the same time, an ambient air inlet 31 provided with a no-return valve 32 is provided at the distal end of the second spacer 30. At the proximal end of the second spacer 30, a straight connector 34 with a mouth piece 35 is positioned, while an exhaled gas outlet 36 (optionally with a filter F) branches perpendicularly off the straight connector 34.

Figure 3:
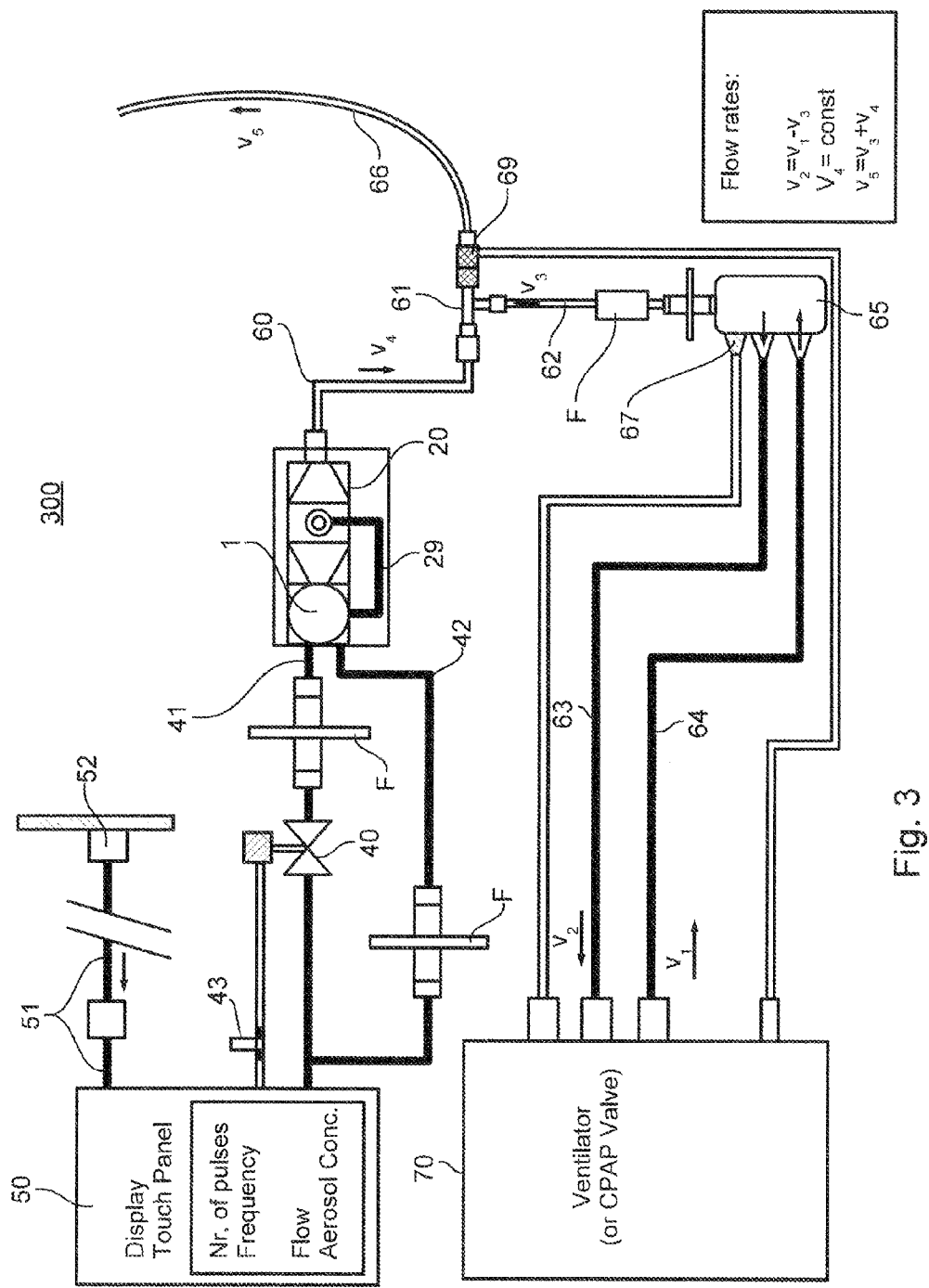
FIG. 3 is schematic view of an embodiment of a system for dosing and aerosolization for use with ventilated infants.

FIG. 3 shows an embodiment of the system for dosing and aerosolization that is particularly suited for acute respiratory therapy of very young children such as infants and neonates. Several components which are the same or are equivalent to those described with respect to FIGS. 1 and 2 bear the same reference numerals and will not be discussed again. The system 300 comprises the device 1 for dosing and aerosolization and the spacer 20, and a controller 50 which is connected to it in the same way as in the embodiment of FIG. 2. Connected to the output of spacer 20 is a ventilator tubing 60 that in turn connects to the first port of a T-piece 61. Further, in this embodiment a ventilator in CPAP mode 70 is provided that supplies respiratory gas via respiratory gas line 64 to a manifold 65 while keeping the ventilator pressure at a constant level. From the manifold 65, a common ventilating line 62 connects to the second port of the T-piece 61. The third port is connected to a nasopharyngeal tube 66 that is introduced through the infant's nose so that its tip is positioned just above the glottis.

Further, a flow rate sensor 67 is disposed at the manifold to measure the gas flow rate V3 of the gas in common line 62. The measurement signals are fed back to the ventilator 70, which directly controls the pressure in line 64 and in line 63 by controlling the respective flow rates, and therefore indirectly controls $V_3$. By means of this pressure control additional flow from the disperser dosing unit causes $V_3$ to be down regulated so that the pressure and hence total flow to the infant (V5) is kept constant.

In addition, an oxygen sensor 69 is provided at the third port of the T-connector 61, monitoring oxygen content of the respiratory gas mixture actually administered to the lungs of the infant. The respective measurement signals are fed back to the ventilator 70, where together with the flow rate information a comprehensive picture of the properties of the supplied respiratory gas mixture is obtained. These properties are then in turn controlled by the ventilator 70. In summary, by connecting the device 1 in parallel with the respiratory system, it becomes possible both to provide oxygen-rich respiratory gas and the correct dose of aerosolized material, such as lung surfactant.

Figure 4:
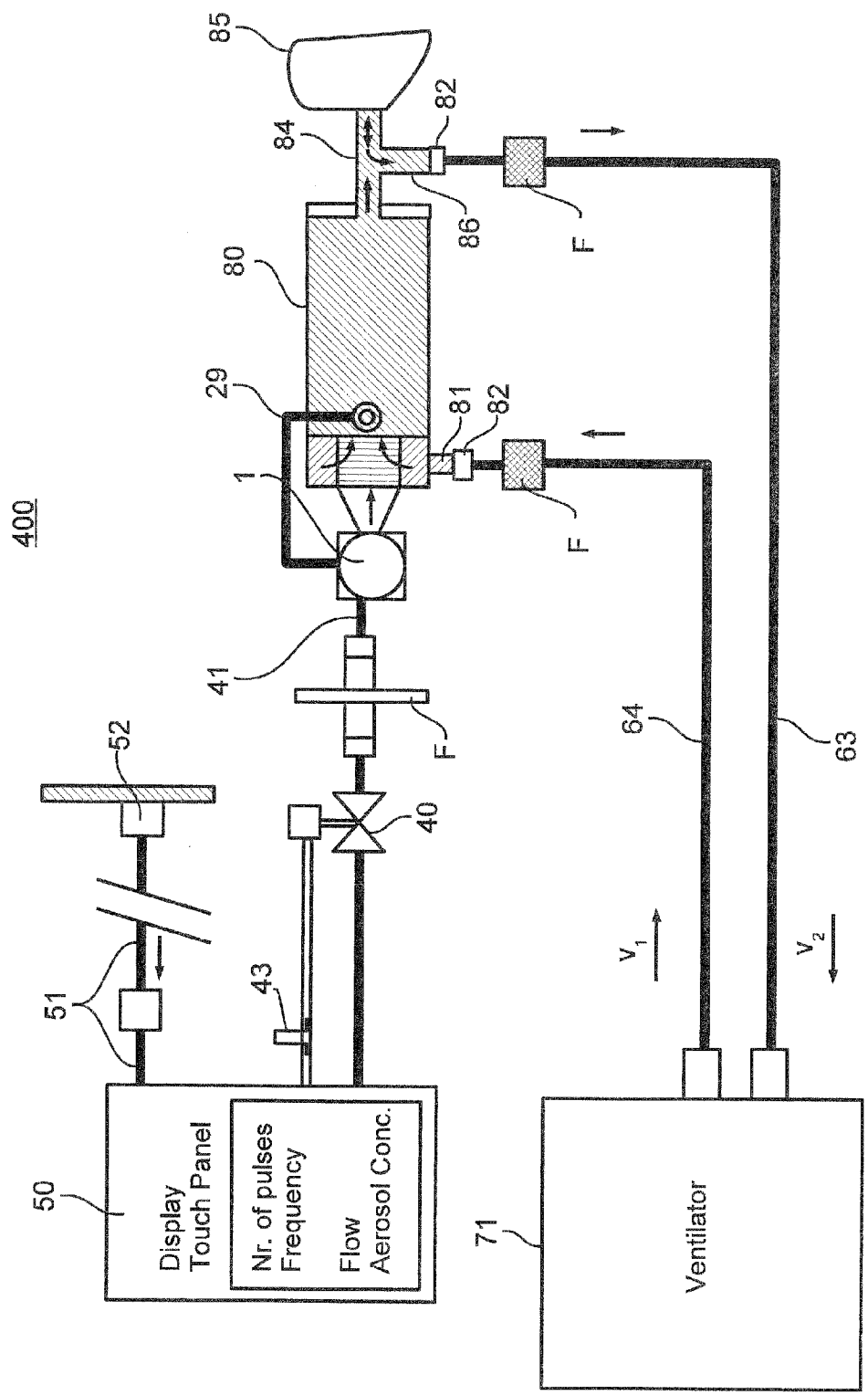
FIG. 4 is schematic view of an embodiment of a system for dosing and aerosolization for use with ventilated adults.

Finally, turning to FIG. 4, another embodiment of a system for dosage and aerosolization is shown. The system 400 is used with ventilated adult patients and comprises the device 1 for dosing and aerosolization, the controller 50, a ventilator 71 and a hollow spacer 80. The controller is connected in the above-described manner to a hospital air supply 52 and via a main connecting line 41 with valve 40 to the device 1, just as described in the foregoing embodiments. However, in this embodiment, the spacer 80 is much larger than spacer 20, both in diameter and in volume, in order to accommodate the needs of an adult ventilated patient. The spacer 80 is connected at its distal end to the proximal attachment piece 2a of the device 1 and has at its proximal end a straight connector 84 leading to a breathing mask 85. A respiratory gas inlet 81 with a non-return valve 82 is disposed laterally on the distal end of the spacer 80 and is connected in the usual manner via a filter and respiratory gas line 64 to the ventilator 71. Similarly, at the proximal side an exhaled gas outlet 86 is connected via a non-return valve 82 and exhaled gas return line 63 to the ventilator.

The amount of aerosolizable material that can be administered with the devices and systems of the present invention exceeds 50 mg and is coupled with a high precision of dosage. On the one hand, the precision allows the use of drugs having a particularly narrow "therapeutic window" and on the other hand the large volumes make the system suitable for use with substances that need to be administered in large quantities. For example, aerosolizable medical substances other than lung surfactant which can be administered by use of the device according to the invention include contrast agents, antibiotics, nucleic acids, retard formulas, peptides/proteins, vaccines, antibodies, insulin, osmotically active substances like mannitol, hydroxyethyl starch, sodium chloride, sodium bicarbonate and other salts, enzymes (e.g. DNAse), N-acetyl cystein, etc.

The invention claimed is:

1. A system for dosing and aerosolization of aerosolizable material, the system comprising:
    a body with an aerosolization channel having a distal attachment portion connectable to a source of carrier gas which provides pressure pulses of the gas to the aerosolization channel and a proximal attachment portion for outputting aerosolized material towards a patient;
    a reservoir for receiving aerosolizable material, the reservoir comprising at least one wall and being connected in a gas-tight manner to the body and in fluid connection with the aerosolization channel;
    a funnel portion tapered towards the aerosolization channel provided in the body between the reservoir and the aerosolization channel;
    an additional piece of pathway for aerosol to traverse configured to introduce expansion space for the pulsed gas stream and thus allow the pressure pulse of the gas arranged to carry the aerosol to the patient to dampen, the additional piece of pathway being a first hollow spacer comprising a distal portion having at least one inner wall tapered towards the proximal attachment portion, and a proximal portion having at least one inner wall and configured to taper towards the patient, with a central cylindrical portion therebetween having at least one inner wall, and the additional piece of pathway further being connected to the proximal attachment portion; and
    a compensation tubing provided between an interior of the first hollow spacer and an interior of the funnel portion, wherein at least one wall of the funnel portion and the at least one inner wall of the distal portion, of the central portion and/or the proximal portion of the first hollow spacer comprise self-exciting membranes that can be put into oscillation by the pressure pulses,
    and wherein corresponding spaces are provided between such self-exciting membranes and an outer wall.

2. The system of claim 1, wherein the reservoir is provided with a top cover and the top cover comprises a self-exciting membrane towards the reservoir.

3. The system of claim 1, wherein a self-exciting membrane is provided in a wall of the aerosolization channel beneath the connection thereof with the reservoir.

4. The system of claim 1, wherein the reservoir and the body are integrally formed.

5. The system of claim 1, wherein the reservoir is connected with the aerosolization channel via a valve.

6. The system of claim 5, wherein the valve is a rotary valve.

7. The system of claim 1, wherein an annular gap is provided between the distal and the central portions of the first hollow spacer, which is connectable to an auxiliary air supply.

8. The system of claim 7, further comprising a second hollow spacer connected proximally to the proximal portion of the first hollow spacer and distally to a mouth piece, the second hollow spacer having an ambient air inlet with a non-return valve provided at the distal end and an exhaled gas outlet provided at the proximal end of the second hollow spacer.

9. The system of claim 1, further comprising a ventilator or a CPAP valve, wherein the proximal portion of the first hollow spacer and the ventilator or CPAP valve are connected via a Y-connector to a patient side respiratory front end.

10. The system of claim 9, wherein an air delivery port of the ventilator and an exhaled gas port of the ventilator are connected to the Y-connector via a manifold.

11. The system of claim 10, wherein a flow sensor is provided at the manifold, and an oxygen sensor is provided at a patient side port of the Y-connector.

12. The system of claim 9, wherein the patient side respiratory front end is a nasopharyngeal tube.

13. The system of claim 9, wherein the first hollow spacer is connected proximally to a respiratory front end,
    wherein the first hollow spacer is further connected at its distal end via a non-return valve to an air delivery port of the ventilator, and is further connected at its proximal end to an exhaled gas port of the ventilator.

14. The system of claim 9, wherein any one of a flow sensor and an oxygen sensor is provided between the ventilator or CPAP valve and the patient side respiratory front end.

15. The system of claim 1, wherein the system further comprises:
    a control box for providing pressure pulses of carrier gas to the aerosolization channel, the control box being connectable to a hospital compressed air supply and connected to the distal attachment portion of the body via a valve,
    wherein the control box is adapted to control the number and frequency of the carrier gas pressure pulses and the flow rate of the carrier gas by controlling the valve.

* * * * *

UNITED STATES PATENT AND TRADEMARK OFFICE
CERTIFICATE OF CORRECTION

PATENT NO. : 8,910,627 B2
APPLICATION NO. : 13/264422
DATED : December 16, 2014
INVENTOR(S) : Peter Iwatschenko et al.

It is certified that error appears in the above-identified patent and that said Letters Patent is hereby corrected as shown below:

In the Claims

Claim 1, Column 11, Line 50: Between "Therebetween" and "at least one inner wall" Please delete the word "haying" and replace with "having".

Signed and Sealed this
Twenty-fourth Day of March, 2015

Michelle K. Lee
*Director of the United States Patent and Trademark Office*